United States Patent [19]

Van den Heuvel et al.

[11] Patent Number: 5,196,224

[45] Date of Patent: Mar. 23, 1993

[54] SUBSTITUTED THIOPHENES, AND FLAVORING AND PERFUME COMPOSITIONS AND FLAVORED AND PERFUMED PRODUCTS WHICH CONTAIN ONE OR MORE SUBSTITUTED THIOPHENES

[75] Inventors: Henry L. A. Van den Heuvel, Bussum; Paulus P. J. M. Jaegers, Hilversum, both of Netherlands

[73] Assignee: Naarden-International N.V., Naarden-Bussum, Netherlands

[21] Appl. No.: 717,994

[22] Filed: Jun. 20, 1991

Related U.S. Application Data

[63] Continuation of Ser. No. 69,119, Jul. 2, 1987, abandoned, which is a continuation-in-part of Ser. No. 901,433, Aug. 28, 1986, abandoned.

[30] Foreign Application Priority Data

Sep. 16, 1985 [NL] Netherlands ............. 8592530

[51] Int. Cl.$^5$ .................................. A23L 1/235
[52] U.S. Cl. ........................ 426/535; 424/49; 549/29; 512/11
[58] Field of Search ........................ 426/535

[56] References Cited

U.S. PATENT DOCUMENTS 3,702,253 11/1972 Winter et al. ............ 426/535
3,979,527 9/1976 Laws et al. ............ 426/600 X

OTHER PUBLICATIONS

Suggett et al., "The Role of Sulphur Compounds in Hop Flavor," European Brewery Convention Congress, 1979, pp. 79-89.

Primary Examiner—Joseph Golian
Attorney, Agent, or Firm—Brumbaugh, Graves, Donohue & Raymond

[57] ABSTRACT

Flavoring and perfume compositions as well as flavored foodstuffs and allied products and also perfumed products characterized by a content of one or more substituted thiophenes with the formula

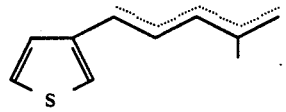

wherein none, one or two of the dotted lines represent a double bond with the proviso that no cumulated double bonds are present.

4 Claims, No Drawings

SUBSTITUTED THIOPHENES, AND FLAVORING AND PERFUME COMPOSITIONS AND FLAVORED AND PERFUMED PRODUCTS WHICH CONTAIN ONE OR MORE SUBSTITUTED THIOPHENES

This application is a continuation of U.S. patent application Ser. No. 07/069,119, filed Jul. 2, 1987, now abandoned which is a continuation-in-part of U.S. patent application Serial No. 901,433 filed Aug. 28, 1986 now abandoned.

BACKGROUND OF THE INVENTION

The invention relates to flavouring and perfume compositions which contain one or more 3-alkyl-, 3-alkenyl- and 3-alkadienyl-substituted thiophenes and to foodstuffs and semiluxuries flavoured with one or more of these compounds or with said compositions and to products perfumed therewith. In addition, the invention relates to some 3-alkyl-, 3-alkenyl- and 3-alkadienyl-substituted thiophenes.

There is an on-going interest in the preparation of synthetic flavours and fragrances and the application thereof in foodstuffs and semiluxuries and in products to be perfumed such as cosmetics, soaps, detergents, household products and the like. This interest is stimulated by the insufficient quantity and often varying quality of natural flavours and fragrances. Although sulphur compounds per se generally do not have a pleasant taste and odour, it has nevertheless emerged that sulphur compounds play an essential role in many natural flavours and odours. It also appears that in many perfumes a somewhat "sulphurous" note is desirable to complete the total odour. There is therefore a requirement for compounds with a clearly pleasant sulphurous odour and flavour note which, however, does not come too strongly to the fore, preferably combined with other, pleasant olfactory properties so that the compounds can easily be combined with known fragrances and flavours.

Surprisingly, it has now been found that 3-substituted thiophenes with the general formula I

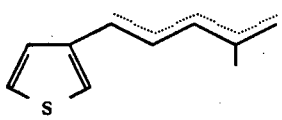

(I)

have organoleptically very valuable properties, as a result of which they are very suitable for use as fragrances or flavours.

In formula I none, one or two of the dotted lines represents a double bond and in particular in a manner such that no cumulated double bonds are present. The compounds represented in this manner may have both the E and the Z configuration.

Such substituted thiophenes are hardly known in the perfume and flavour industry. U.S. Pat. No. 3,702,253 makes mention of 3-vinylthiophene which can be used as a flavour in foodstuffs and drinks and has a hydrocarbon-like odour or taste.

Said compound, however, has chemical structure quite a different the 3-(4-methylpentyl)thiophene, 3-(4-methylpentenyl)thiophene and 3-(4-methyl-pentadienyl)-thiophene of the present invention.

3-(4-Methylpent-3-enyl)thiophene has been detected by various investigators in hop oil (see A. Suggett, M. Moir, J. C. Seaton, Proceedings of the European Brewery Convention Congress, Berlin, 1979, pages 79-89; T. L. Peppard, J. A. Elvidge, Chem. & Ind. 1979, pages 552-3; S. Araki, Y. Butsugan, Bull. Chem. Soc. Japan, 56 (1983), pages 1446-9 and J. A. Elvidge, S. P. Jones, J. Chem. Soc. Perkin I, 1982, pages 1089-94). In the last publication the compound is described as a "pungent oil". Suggett and his coworkers, who first detected this and some other sulphur compounds in hop, report that they give an undesirable flavour when added to beer.

The other compounds according to the invention were hitherto unknown.

It was not possible to suppose therefore that the compounds according to the invention would have such valuable and varied organoleptic properties which, in addition to a general, but not very pronounced sulphurous note contain, inter alia, flowery, green, spicy, citrus-like, malty and caramel-like odour and taste notes. Thus, the above-mentioned 3-(4-methylpent-3-enyl)thiophene is characterized by a pleasant green and citrus-like odour and a taste which clearly has citrus aspects and the organolepsis of Z-3-(4-methylpenta-1,3-dienyl)-thiophene exhibits a green and fresh-flowery character, but that of E-3-(4-methylpenta-1,3-dienyl)thiophene exhibits a spicy, malty, caramel-like character.

The compounds according to the invention can be used as such as flavours and fragrances, or they can first be mixed with suitable carriers or diluents. They can also be combined with other single compounds or with mixtures, for example with ethereal oils, in a usual manner for the formation of flavouring or perfume compositions. In this connection the terms "flavouring composition" and "perfume compositions" mean mixtures of flavours or fragrances respectively and/or ethereal oils, if desired dissolved in a suitable solvent or mixed with a powdered substrate or processed to form a powdered product and used to impart a desired taste or odour to products of all types, or to reinforce or to improve the taste or odour which these products already have. Products to be flavoured are foodstuffs and semiluxuries, by which in this connection are meant: solid or liquid products intended for human consumption, including tobacco products, medicines and toothpaste. Products to be perfumed are, for example, soaps, detergents, air-fresheners, room sprays, pomanders, candles, cosmetics such as creams, ointments, toilet waters, pre- and after-shave lotions, talcum powders, hair-care agents, body deodorants and antiperspirants.

Basic perfume and flavouring substances which can be advantageously combined with the compounds according to the invention are, for example, natural products such as extracts, ethereal oils, absolutes resinoids, resins, concretes, etc., but also synthetic basic substances such as hydrocarbons, alcohols, aldehydes, ketones, ethers, acids, esters, acetals, ketals, nitriles, etc., including saturated and unsaturated compounds, aliphatic, carbocyclic and heterocyclic compounds.

Such basic materials are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in T. E. Furia et al., CRC Fenaroli's Handbook of Flavor Ingredients, 2nd edition (Cleveland, CRC Press Inc., 1975).

Examples of fragrances which can be used in combination with the compounds according to the invention are geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butyl cyclohexyl acetate, isononyl acetate, vetiveryl acetate, vetiverol, α-hexylcinnamaldehyde, 2-methyl-3-(p-tert-butylphenyl) propanal, 2-methyl-3-(p-isopropyl-phenyl)propanal, 3-(p-tert-butylphenyl)propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptyl-cyclopentanone, 3-methyl-2-pentyl-2-cyclopentenone, n-decanal, n-dodecanal, 9-decenol-1, phenoxyethyl isobutyrate, phenylacetaldehyde dimethylacetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks, tetralin musks, isochroman musks, macrocyclic ketones, macrolactone musks, ethylene brassylate, aromatic nitromusks.

Auxiliary materials and solvents which can be used in perfume compositions which contain compounds according to the invention are, for example: ethanol, isopropanol, diethyleneglycol monoethyl ether, diethylphthalate etc. Such auxiliary materials and solvents for aroma compositions are, for example: ethanol, diethyleneglycol monoethyl ether, propylene glycol, glycerol and triacetin.

The quantities of the compounds according to the invention to be used may be strongly divergent and depend, inter alia, on the product in which the compounds are used and on the nature and the quantity of the other components of a flavouring or perfume composition.

In most cases a quantity of 0.05 parts by weight per million of a compound according to the invention in foodstuffs and semiluxuries will already be perceptible. In concentrated flavouring compositions a quantity of up to 5% by weight can be used with advantage in some cases.

In concentrated perfume compositions quantities of 100 parts by weight per million may already have a perceptible effect on the odour impression. On the other hand, to achieve special odour effects it is also possible to use a quantity of 5% by weight or even more in a composition. In products perfumed with the aid of perfume compositions these concentrations are proportionally lower, depending on the quantity used of the composition in the finished product.

The compounds according to the invention can be prepared according to methods usual for such compounds, for example by the Wittig reaction of 3-thienylcarbaldehyde or 3-thienylacetaldehyde with an ylide prepared from a suitably chosen alk(en)yltriphenylphosphonium halide. Insofar as it is possible for the compounds according to the invention to be (Z)- and (E)-isomers, the above-mentioned synthesis methods yield a mixture of said isomers. The ratio of isomers in the mixture can be influenced by changes in the reaction procedure. Thus, more of the (Z)-isomer is obtained if the reaction is carried out in a nonpolar solvent and, on the other hand, more of the (E)-isomer is obtained in polar solvents and/or in the presence of lithium salts, for example by making use of a lithium base for the preparation of the ylide. The Wittig reaction is described in J. March, Advanced Organic Chemistry, 2nd edition, pages 864–872, in particular page 870, and in the literature mentioned therein.

The 4-methylpentyl and some 4-methylpentenyl compounds may be prepared by a Wurtz-type reaction between 3-halomethylthiophene, a 3-methylbut(en)yl halide and magnesium.

3-(4-Methylpent-3-enyl)thiophene can be prepared according to the instructions of S. Araki and Y. Butsugan (see above) or of A. Corvers, J. H. van Mil, M. M. E. Sap and H. M. Buck, Rec. Trav. Chim. Pays BAS, 96 (1977), pages 18–22.

Isomeric mixtures obtained in the preparation of compounds according to the invention may be separated into the separate isomers in a conventional manner, for example by means of preparative GLC. As a rule, however, such a separation is not necessary and the isomeric mixture can be used with advantage as a flavouring or perfume.

The following examples are exclusively intended to illustrate the method according to the invention and the synthesis of the compounds according to the invention. The invention is, however, not limited thereto.

EXAMPLE I

Preparation of 3-(4-methylpent-3-enyl)thiophene 550 g of cyclohexane, 231 g of 3-methylthiophene and 5 g of azoisobutyronitrile were introduced into a 2-liter reaction flask. The mixture was heated while stirring thoroughly until it refluxed, after which a mixture of 437 g of N-bromosuccinamide and 5 g of azoisobutyronitrile was added at a rate such that the reaction mixture continued to reflux.

After everything had been added, the reaction mixture was cooled to 10° C., then the precipitated succinamide was filtered off and washed with cyclohexane. The combined filtrate was evaporated down under reduced pressure and the evaporation residue was distilled from 2 g of calcium carbonate. 217 g (52%) of 3-bromomethylthiophene were obtained; b.p. 42°–48° C./0.2 kPa.

217 g of 3-bromomethylthiophene, 513 g of prenylchloride, 117 g of copper (I) iodide and 2 kg of tetrahydrofuran were introduced into a 4-liter reaction flask. 750 g of magnesium shavings were then added in small portions at a rate such that the temperature of the reaction mixture did not rise above 30°. If the temperature rises were to great, the reaction mixture was temporarily cooled. The first portion of magnesium was activated by subliming an iodine crystal onto it. After all the magnesium had been added, a check was made by means of GLC as to whether bromomethylthiophene or prenyl chloride was still present. It was possibly necessary to add more magnesium. The mixture was then stirred for a further hour at 40° C. and after that poured out into a mixture of 180 g of ammonium chloride, 1 liter of water and 500 g of ice, and stirred.

The aqueous layer was separated and extracted with 800 g of cyclohexane. The combined organic layers were evaporated down under reduced pressure. A fraction of 142 g boiling at 48°–60° C./0.15 kPa, was collected. This was fractionated under reduced pressure, 112 g of 3-(4-methylpent-3-enyl)thiophene being collected; b.p. 68° C./0.3 kPa (yield 55%).

EXAMPLE II

Preparation of 3-(4-methylpenta-1,3-dienyl)thiophene

Prenyltriphenylphosphonium chloride was prepared according to the instructions of R. Rüegg, U. Schweiter, G. Rijser, P. Schudel and O. Isler; Helv. Chim. Acta., 44. 994 (1961).

73.4 of Prenyltriphenylphosphonium chloride, 7.8 g of sodium amide and 260 ml of dry tetrahydrofuran were introduced into a 1-liter reaction flask. The reaction mixture was kept under a dry nitrogen atmosphere, stirred at room temperature for 30 minutes and then cooled to approx. −15° C. A solution of 19.8 g of 3-thienylcarbaldehyde in 50 ml of dry tetrahydrofuran was then added in measured quantities in a manner such that the temperature of the reaction mixture remained below −10° C. After this addition, the reaction mixture was stirred for a further 4 hours at room temperature. 200 ml of water were then added, after which the organic layer was separated. The aqueous layer was extracted 3 times with ether. The combined organic layers were dried over magnesium sulphate and then evaporated down under reduced pressure. From the evaporation residue the precipitated triphenylphosphine oxide was removed by boiling up five times with petroleum ether and filtering. The filtrate was evaporated down, 22 g of evaporation residue being obtained which was distilled under reduced pressure. 12 g (42%) of 3-(4-methylpenta-1,3-dienyl)thiophene, b.p. 96°-97° C./0.15 kPa were obtained consisting of a mixture of 60% (Z)-isomer and 40% (E)-isomer. The mixture exhibited a spicy and fresh-flowery character and was as such very suitable for use as a flavour or fragrance.

It was possible to separate it into the two pure components by means of GLC through a packed column containing 10% DEGS as the stationary phase (2 m, column temperature 165° C., gas flow rate 60 ml/min), the (Z)-isomer being obtained first.

(E)-isomer: m.p. 31°-32° C.

NMR (CCl4, 100 MHz, δ in ppm with respect to TMS): 1.81 (6H, broad s); 5.82 (1H, broad d, J=10 Hz); 6.30 (1H, d, J=15 Hz); 6.67 (1H, dd, J=10 and 15 Hz); 6.97 (1H); 7.13 (2H).

(Z)-isomer: n 20/D=1.6075.

NMR: 1.79 (3H, broad s); 1.81 (3H, broad s); 6.0–6.4 (3H, m); 6.9–7.2 (3H, m).

EXAMPLE III

Preparation of 3-(4-methyl-pent-1-enyl)-thiophene

A mixture of 20.7 g (0.05 mol) isoamyl-triphenylphosphonium bromide, 2.0 g (0.05 mol) NaNH2 and 75 ml dry diethyl ether was stirred and heated to 35° C. for 45 minutes under an atmosphere of dry nitrogen. Thereafter a solution of 4.9 g (0.044 mol) freshly distilled thien-3-yl carbaldehyde in 50 ml of dry diethyl ether was added and the reaction mixture was stirred for 8 hours at 20° C. 100 ml of water was added and the mixture was worked up and the triphenylphosphine oxide removed as described in Example II. Distillation of the reaction product yielded 5.1 g (70%) 3-(4-methyl-pent-1-enyl)-thiophene as a mixture of 90% Z and 10% E isomer.

Boiling point: 64°-65° C./0.13 kPa. $n_D^{20} = 1.5328$

EXAMPLE IV

Preparation of 3-(4-methylpentyl)-thiophene

To 12 g of freshly distilled 3-(4-methyl-pent-3-enyl)-thiophene dissolved in 150 ml ethanol was added 1 g of 5% Pd/C hydrogenation catalyst. The mixture was hydrogenated at atmospheric pressure in 72 hours. The catalyst was filtered of, the solvent evaporated and the residue distilled, yielding 8 g (66%) 3-(4-methylpentyl)-thiophene. Boiling point: 65°-66° C./0.13 kPa. $n_D^{20} = 1.4962$.

The compound has a green, hyacinth-like and slightly fruity odour and a floral green flavour.

EXAMPLE V

Preparation of 3-(4-methyl-penta-1,4-dienyl)-thiophene 32 ml of a 1.6 M solution of butyl lithium in hexane was added to a mixture of 25.2 g (0.055 mol) isoprenyl-triphenylphosphonium iodide and 65 ml dry tetryhydrofuran at −5° C. under an atmosphere of dry nitrogen. After stirring the mixture for 45 minutes it was cooled to −50° C. and a solution of 5.6 g (0.05 mol) freshly distilled thien-3-yl carbaldehyde in 30 ml dry tetryhydrofuran was added gradually over 30 minutes. The reaction mixture was stirred for another hour at −30° C. When the mixture had reached 0° C., 100 ml of ice water was added and the mixture was worked up and the triphenylphosphine oxide removed as described in Example II. Distillation of the reaction product yielded 4.1 g (50%) 3-(4-methyl-penta-1,4-dienyl)-thiophene as a mixture of 50% Z and 50% E isomer.

Boiling point: 87°-90° C./0.13 kPa. $n_D^{20} = 1.5569$

The mixture has a sweet green odour resembling ripe tomatoes and a green and mushroom-like flavour.

EXAMPLE VI

A grapefruit flavouring for a soft drink was prepared according to the recipe below:
1.7 g of grapefruit juice oil
4.0 g of lime extract
17.0 g of orange extract
110.0 g of grapefruit oil extract
390.0 g of ethanol The above components were mixed and stirred until quite homogeneous. The mixture was then made up to 1 kg with demineralized water while still stirring.

From the above mentioned flavouring a grapefruit drink was prepared by adding 2 g of the aroma to 1 liter of water containing carbonic acid.

A grapefruit drink was prepared in the same manner starting from a grapefruit flavouring that in addition to the above mentioned components contained also 0.3 g of 3-(4-methylpent-3-enyl)thiophene per kg of flavouring.

Both grapefruit drinks were compared by a panel of experts. It was generally agreed that the grapefruit drink which contained 3-(4-methylpent-3-enyl)thiophene has a more powerful and more complete grapefruit taste.

EXAMPLE VII

A perfume composition for a man's cologne was prepared according to the recipe below:

| | |
|---|---|
| Acetyl cedrene | 150 parts by weight |
| Bergamot oil, furocoumarin-free | 100 " |

-continued

| | | |
|---|---|---|
| Linalyl acetate | 50 | " |
| Lavandin oil | 50 | " |
| Geranium oil, bourbon | 50 | " |
| Lemon oil | 50 | " |
| Coumarin | 30 | " |
| Lavendar oil, French | 30 | " |
| 2-Methyl-3-(p-tert-butylphenyl)-propanal | 25 | " |
| Heliotropin | 20 | " |
| Dihydromyrcenol | 20 | " |
| 11-Oxahexadecanolide | 20 | " |
| Lime Oil | 20 | " |
| Vetiveryl acetate | 20 | " |
| Petitgrain oil | 20 | " |
| Methyl 2,4-dihydroxy-3,6-dimethylbenzoate | 10 | " |
| Coriander oil | 10 | " |
| Sandelwood oil, East Indian | 10 | " |
| Eugenol | 10 | " |
| Sagebrush oil | 10 | " |
| Methylnonylacetaldehyde* | 10 | " |
| Methylchavicol | 5 | " |
| 3-(4-Methylpent-3-enyl)thiophene* | 20 | " |
| | 750 | parts by weight |

*10% solution in dipropylene glycol

We claim:

1. A flavoring composition comprising greater than 0.03% of one or more compounds of the formula

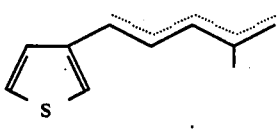

wherein the dotted lines represent single or double bounds, with the provisos that no more than two of the dotted lines represent double bonds, and no two double bonds are adjacent; together with
   (a) at least one additional flavoring substance; and
   (b) customary auxiliary materials.

2. A flavoring composition according to claim 1, wherein the composition includes grapefruit oil extract.

3. A flavoring composition according to claim 1, comprising 0.03% to 5% of the substitute thiophene compounds.

4. A flavoring composition according to claim 1, wherein the substituted thiophene compound is 3-(4-methyl-pent-3-enyl)thiophene.

* * * * *

UNITED STATES PATENT AND TRADEMARK OFFICE
CERTIFICATE OF CORRECTION

PATENT NO. : 5,196,224

DATED : March 23, 1993

INVENTOR(S) : Van Den Heuvel et al.

It is certified that error appears in the above-identified patent and that said Letters Patent is hereby corrected as shown below:

On the title page, item [30]: The number of Dutch Priority application, "8592530" should be --8502530--;

Col. 1, line 64, "quite a different" should read --quite different from--;

Col. 4, bridging lines 9-10, "copounds" should read --compounds--;

Col. 4, line 54, "to great" should read --too great--;

Col. 5, line 56, "NaNH2" should read --NaNH$_2$--;

Col. 6, line 9, "of" should read --off--;

Col. 8, line 12, "bounds" should read --bonds--.

Signed and Sealed this

First Day of November, 1994

Attest:

BRUCE LEHMAN

Attesting Officer   Commissioner of Patents and Trademarks